(12) United States Patent
Yarmush et al.

(10) Patent No.: US 9,535,056 B2
(45) Date of Patent: Jan. 3, 2017

(54) IMMUNE SYSTEM MODELING DEVICES AND METHODS

(75) Inventors: Martin L. Yarmush, Newton, MA (US); Robert Freedman, Beverly Hills, CA (US); Aurelia Del Bufalo, Paris (FR); Silvia Teissier, Rueil Malmaison (FR); Jean-Roch Meunier, Aulnay sous Bois (FR)

(73) Assignee: L'OREAL, Paris (FR)

( * ) Notice: Subject to any disclaimer, the term of this patent is extended or adjusted under 35 U.S.C. 154(b) by 615 days.

(21) Appl. No.: 12/812,225

(22) PCT Filed: Jan. 10, 2009

(86) PCT No.: PCT/US2009/030686
§ 371 (c)(1),
(2), (4) Date: Oct. 5, 2010

(87) PCT Pub. No.: WO2009/089512
PCT Pub. Date: Jul. 16, 2009

(65) Prior Publication Data
US 2011/0027804 A1 Feb. 3, 2011

Related U.S. Application Data

(60) Provisional application No. 61/020,310, filed on Jan. 10, 2008.

(51) Int. Cl.
| C12Q 1/02 | (2006.01) |
| G01N 33/50 | (2006.01) |
| C12M 3/06 | (2006.01) |
| C12M 1/00 | (2006.01) |

(52) U.S. Cl.
CPC ............ G01N 33/505 (2013.01); C12M 23/16 (2013.01); C12M 23/58 (2013.01); G01N 33/5044 (2013.01)

(58) Field of Classification Search
None
See application file for complete search history.

(56) References Cited

U.S. PATENT DOCUMENTS

| 4,436,824 | A | | 3/1984 | Bishop | |
| 4,835,102 | A | * | 5/1989 | Bell et al. | 435/29 |
| 5,627,025 | A | * | 5/1997 | Steinman et al. | 435/5 |
| 5,962,477 | A | * | 10/1999 | Mak | 514/327 |
| 6,653,124 | B1 | | 11/2003 | Freeman | |
| 6,921,660 | B2 | * | 7/2005 | Kirk et al. | 435/287.2 |
| 7,709,256 | B2 | | 5/2010 | Warren | |
| 7,771,999 | B2 | | 8/2010 | Warren | |
| 7,785,806 | B2 | | 8/2010 | Warren | |
| 7,785,883 | B2 | | 8/2010 | Warren | |
| 7,855,074 | B2 | | 12/2010 | Warren | |
| 8,030,070 | B2 | | 10/2011 | Sanchez-Schmitz | |
| 2003/0082795 | A1 | * | 5/2003 | Shuler et al. | 435/286.1 |
| 2005/0191743 | A1 | | 9/2005 | Wu | |
| 2005/0282148 | A1 | | 12/2005 | Warren | |
| 2006/0078540 | A1 | | 4/2006 | Warren | |
| 2007/0015136 | A1 | | 1/2007 | Sanchez-Schmitz | |

FOREIGN PATENT DOCUMENTS

| WO | 2005104755 A2 | 11/2005 |
| WO | 2006/037033 A2 | 4/2006 |
| WO | 2006037033 A2 | 4/2006 |
| WO | 2007/021343 A2 | 2/2007 |
| WO | 2007021343 A2 | 2/2007 |
| WO | 2007108835 A2 | 9/2007 |

OTHER PUBLICATIONS

Dietz AB et al. 2004. Imatinib mesylate inhibits T-cell proliferation in vitro and delayed-type hypersensitivity in vivo. Blood 104: 1094-1099.*
Caux C et al. 1999. Respective involvement of TGF-b and IL-4 in the development of Langerhans cells and non-Langerhans dendritic cells from CD341 progenitors. J Leukoc. Biol 66: 781-791.*
Dudda JC et al. 2004. T Cell Trafficking to Inflamed Skin: Role for Tissue Microenvironment and Dendritic Cells in Establishment of T Cell-Homing Subsets. J Immunol 172: 857-863.*
Matsubara, Y., et al, Biosensors and Bioelectronics, vol. 19, pp. 741-747 (2004).
Celluzzi, C. M., Journal of Hematotherapy & Stem Cell Research, vol. 12, pp. 575-585 (2003).
Matsubara, Yasutaka, et al., Biosensors and Bioelectronics, vol. 19, pp. 741-747 (2004).
Sheridan, R. L., Burns, vol. 27, pp. 421-424 (2001).

* cited by examiner

*Primary Examiner* — Lora E Barnahart Driscoll
(74) *Attorney, Agent, or Firm* — Polsinelli PC

(57) ABSTRACT

Devices and methods are provided for detecting an immune reaction to a test agent using an immune modeling system comprising a barrier component configured to culture a biological barrier, an immune component configured to culture immune cells, and one or more inter-component microfluidic connections between the barrier component and the immune component. The system provides for culturing a biological barrier in the barrier component of the system, culturing immune cells in the immune component of the system, applying the test agent to the biological barrier, and monitoring the immune cells to detect an immune reaction to the test agent.

22 Claims, 9 Drawing Sheets

IMMUNE SYSTEM MODELING DEVICES AND METHODS

CROSS-REFERENCE

This application claims the benefit of U.S. Provisional Application No. 61/020,310, filed Jan. 20, 2008, which application is incorporated herein by reference.

BACKGROUND OF THE INVENTION

An organism's immune system in one aspect serves to protect it from infection, generally through an innate immune system and an adaptive immune system. On a simple level, organisms rely on physical barriers to prevent pathogens such as bacteria and viruses from entering them. In the event that a pathogen breaches these barriers, the innate immune system is at the ready to provide an immediate, but non-specific response. On a more complex level, when pathogens evade the innate response, some animals are equipped with a third element, the adaptive immune system.

Several types of barriers protect organisms from infection, including mechanical, chemical and biological barriers. The skin of an animal is an example of a biological barrier on the front line of exposure environmental agents an organism might encounter. Composite skin replacement using cultured autologous keratinocytes on acellular allogenic dermis has been used as a skin substitute with promise for burn victim patients (Robert L. Sheridan et al. Burns 2000. 27: 421-424).

Phagocytosis is an important feature of cellular innate immunity. Cells classified as phagocytes are able to engulf, or consume, agents, pathogens or particles. Phagocytes routinely patrol the animal body, e.g., in the skin, seeking out pathogens.

Dendritic cells (DC) are phagocytes found associated with tissues of an animal exposed to the environment. Dendritic cells can be found, for example, in the skin, cornea, nose, lungs, gastrointestinal tract and genitourinary tract. Dendritic cells are known as potent antigen-presenting cells involved in the induction of T cell-mediated immune responses. One important dendritic cell type is Langerhans cells. In recent years serum-free, closed culture systems for establishing and maintaining dendritic cells have been developed (Christina M. Celluzzi and Craig Welbon. 2003. Journal of Hematotherapy & Stem Cell Research., 12(5): 575-585).

Hypersensitivity is a type of immune response causing damage to an animal's own tissues. (Ghaffar, Abdul (2006). Immunology—Chapter Seventeen: Hypersensitivity Reactions. Microbiology and Immunology On-Line Textbook. USC School of Medicine; available at http://pathmicro.med.sc.edu/ghaffar/hyper00.htm; last visited Jan. 10, 2008) Hypersensitivity reactions are divided into four classes referred to as Type I-IV. (supra) Type I hypersensitivity involves an immediate or anaphylactic reaction, often associated with allergy and is mediated by IgE released from mast cells and basophils. (supra) Type II hypersensitivity or antibody-dependent (or cytotoxic) hypersensitivity is mediated by IgG and IgM antibodies. (supra) Type III hypersensitivity reactions can be triggered by immune complexes (including aggregations of antigens, complement proteins, and IgG and IgM antibodies) deposited in various tissues. (supra) Type IV hypersensitivity is referred to as cell-mediated or delayed type hypersensitivity and is involved in many autoimmune and infectious diseases, but may also involve contact dermatitis (e.g., poison ivy). (supra) Hypersensitivity reactions are mediated by, e.g., T cells, monocytes, and phagocytes (including dendritic cells and macrophages).

Understanding the interplay of environmental agents the immune system and hypersensitivity of an organism is both medically and commercially relevant.

SUMMARY OF THE INVENTION

In an aspect, an immune modeling device is disclosed that comprises: a barrier component configured to culture a biological barrier; an immune component configured to culture immune cells; and one or more inter-component microfluidic connections between the barrier component and the immune component. The barrier component of the immune modeling device can further comprise a matrix configured to support cell growth.

In an embodiment, the immune modeling device further comprises an optical observation component configured to view cells within the device. Observation of the cells may include cell movement or proliferation of T-cells or a combination of both. The cell movement can be the movement of immune cells, such as dendritic cells, from one compartment to another compartment. The optical observation component may be located in either compartment or in the inter-component microfluidic connections.

In one embodiment, the device comprises multiple immune modules multiplexed together with inter-connecting microfluidic channels for high throughput screening.

Another aspect of the disclosure includes a method of detecting an immune reaction to a test agent comprising: providing an immune modeling system comprising a barrier component configured to culture a biological barrier, an immune component configured to culture immune cells, and one or more inter-component microfluidic connection between the barrier component and the immune component; culturing a biological barrier in the barrier component of the system; culturing immune cells in the immune component of the system; applying the test agent to the biological barrier; and monitoring the immune cells to detect an immune reaction to the test agent.

A biological barrier for use in the device and method can be selected from the group consisting of skin, cornea, lining of the lungs, lining of the gastrointestinal tract, lining of the genitourinary tract and artificial skin. In an embodiment, a biological barrier is artificial skin comprising cultured keratinocytes. A biological barrier can also further comprise a dermal layer. In an embodiment, an immune reaction detected is delayed type contact hypersensitivity.

The immune cells can be any immune cell, such as T-cells and dendritic cells or immune cells from lymph nodes. In an embodiment, the immune cells comprise T-cells and the biological barrier comprises artificial skin and further comprises dendritic cells. In another embodiment, the only cells included in the immune component comprise T-cells and during the evaluation dendritic cells may migrate into the immune component as an indication of hypersensitivity in response to the test agent.

The device may be utilized to evaluate test agents for their capacity to cause an immune or hypersensitivity reaction. Some of the test agents that one may test include a drug, a cosmetic, nutriceutical, synthetic chemical, fragrance, lubricant, soap, shampoo, hair product, sunscreen, lotion or oil.

Monitoring immune cells can comprise monitoring T cell proliferation. In another embodiment, monitoring the immune cells comprises monitoring dendritic cell migration.

One or more optical observation windows may be utilized in one embodiment to monitor the rate or amount of cells and/or the rate or amount of T-cell proliferation. Other means may be used to monitor the migration of dendritic cells and/or the proliferation of the T-cells.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
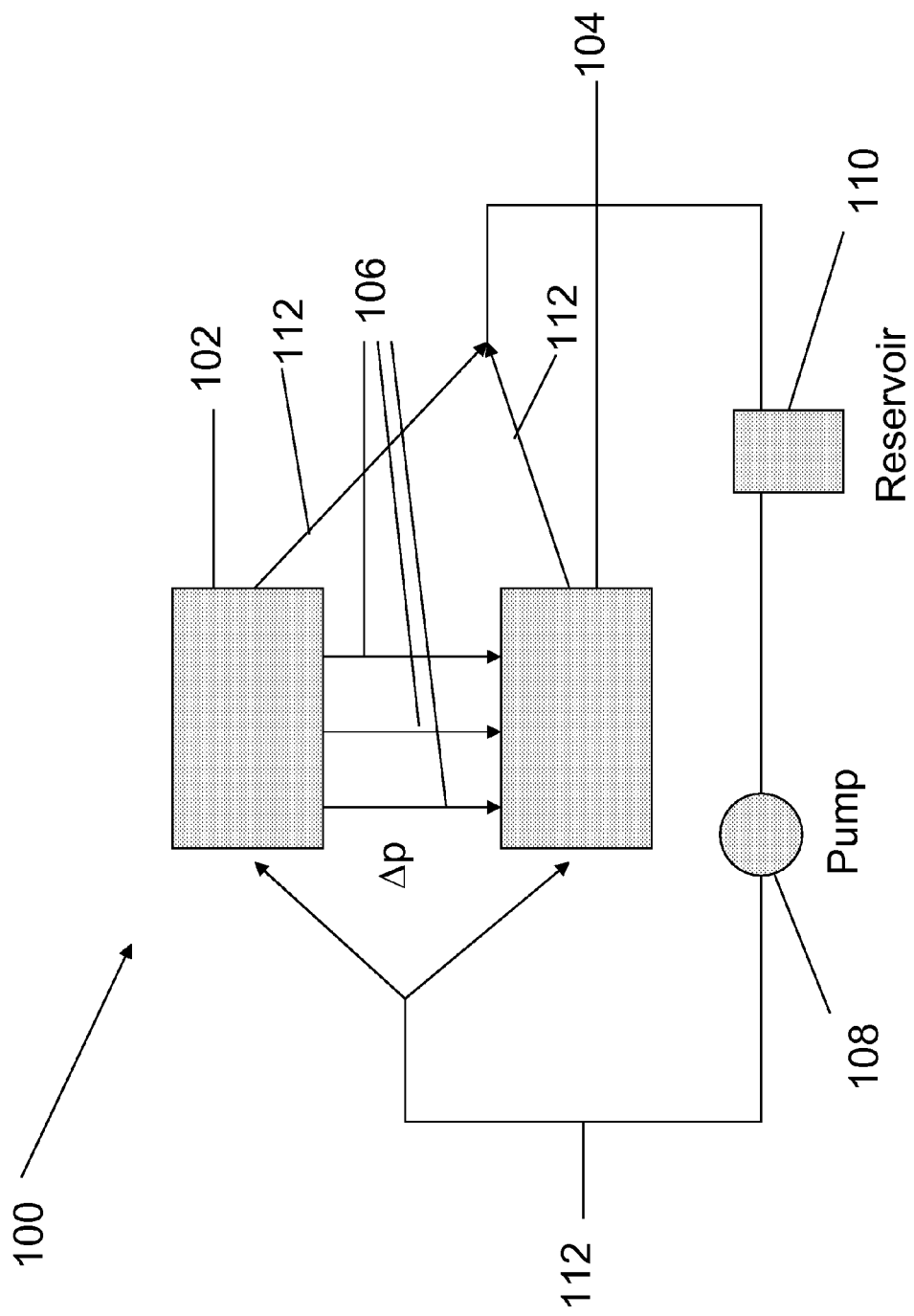
FIG. 1 is a schematic of one embodiment the immune modeling system.

The inventions described herein relate to modeling immune function in biological barriers. Exemplary biological barriers include but are not limited to the skin, cornea, lining of the lungs, lining of the gastrointestinal tract, and lining of the genitourinary tract of animals and humans.

Before the present inventions are described in further detail, it is to be understood that these inventions are not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise.

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention, as are ranges based thereon. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The devices and methods disclosed herein are useful, for example, for use in drug discovery and development and for consumer and industrial product testing including in vivo-surrogate testing.

In response to European Council Directive 76/768/EEC (which bans cosmetics testing on animals and marketing of such products, when alternatives to animal testing are available, and sets a complete ban on cosmetics testing on animals by 2009 and by 2013 for three specific categories), the need for rigorous and predictive forms of in vitro testing of cosmetics has reached a new level of urgency. Described herein is a reliable alternative to the mouse Local Lymph Node Assay ("LLNA"). In the mouse LLNA, following exposure to a sensitizing test substance, lymphocyte proliferation occurs in the local lymph node. The LLNA measures increased proliferation of lymphocytes in the auricular lymph nodes (which drain the ears—the site of exposure). Proliferation can be assessed using LLNA by measuring [3H] thymidine incorporation into the DNA of lymph node cells. Alternatively proliferation can be assessed by measuring incorporation of the thymidine analog, bromodeoxyuridine (BrdU) into the DNA of lymph node cells using flow cytometric methods).

Integrated Immune System Modeling:

FIG. 1 is an illustration of one aspect of the immune modeling system disclosed herein. As shown, immune modeling system 100 can include a barrier component 102, in fluid communication with an immune component 104 by way of inter-component microfluidics 106. Although only one barrier component 102 and one immune component 104 are illustrated, it is envisioned that a plurality of each component can be arranged in fluid communication. Similarly, although three inter-compartment microfluidics 106 are illustrated, it is envisioned that a single or a plurality of inter-compartment microfluidics can be employed to provide fluid communication. As such, it is envisioned that parallel or massively parallel arrangements of fluidically communicating barrier components 102 and immune components 104 are possible (not shown).

As further shown in FIG. 1, microfluidics 112 are provided for fluid communication to the barrier component 102 and immune component 104 from a reservoir 110 (e.g., for media) and a pump/controller 108 (e.g., for providing and controlling fluid flow, including recirculation of fluid in system 100). It is envisioned that system 100 can include a plurality of pump/controller 108 features and a plurality of reservoir 110 features as desired. In addition, the system can include one or more valves in the microfluidics or inter-compartment microfluidics as needed to control fluid flow (not shown).

In one aspect an in vitro delayed type contact hypersensitivity device and methods of use thereof are provided. In a particular embodiment the immune modeling system provides an in vitro surrogate for LLNA. The system can include, for example, 1) a viable epidermis to provide barrier function and skin metabolism, 2) a dendritic cell/Langerhans cell compartment within which these cells can be activated, 3) and a T cell compartment that will allow for T cell activation by migrating, activated dendritic cells (e.g., Langerhans cells). Together these components as well as other features can make up an immune system model that is an in vitro surrogate for LLNA and useful, for example, for measuring delayed type contact hypersensitivity.

Also illustrated in FIG. 1 is an example pump 108 and reservoir 110 for providing liquid, such as media, at least one of a barrier component 102 and an immune component 104. A pump 108 and reservoir 110 can be in fluidic communication with the components through microfluidics 112, or a plurality of microfluidics 112. The microfluidics 112 can also comprise a recirculation feature. It is also envisioned herein that a pump 108 and reservoir 110 are in fluidic communication with a component by any method, such as larger size fluidic components, for example, a pipe. In an embodiment, a pump 108 is controlled automatically or by a protocol from an internal or external source or manually by a user.

In one embodiment, the microfluidic microchannels utilized to connect the compartment containing the biological barrier to the compartment containing the immune or T-cells may be less than about 10 microns in width and height.

Figure 2:
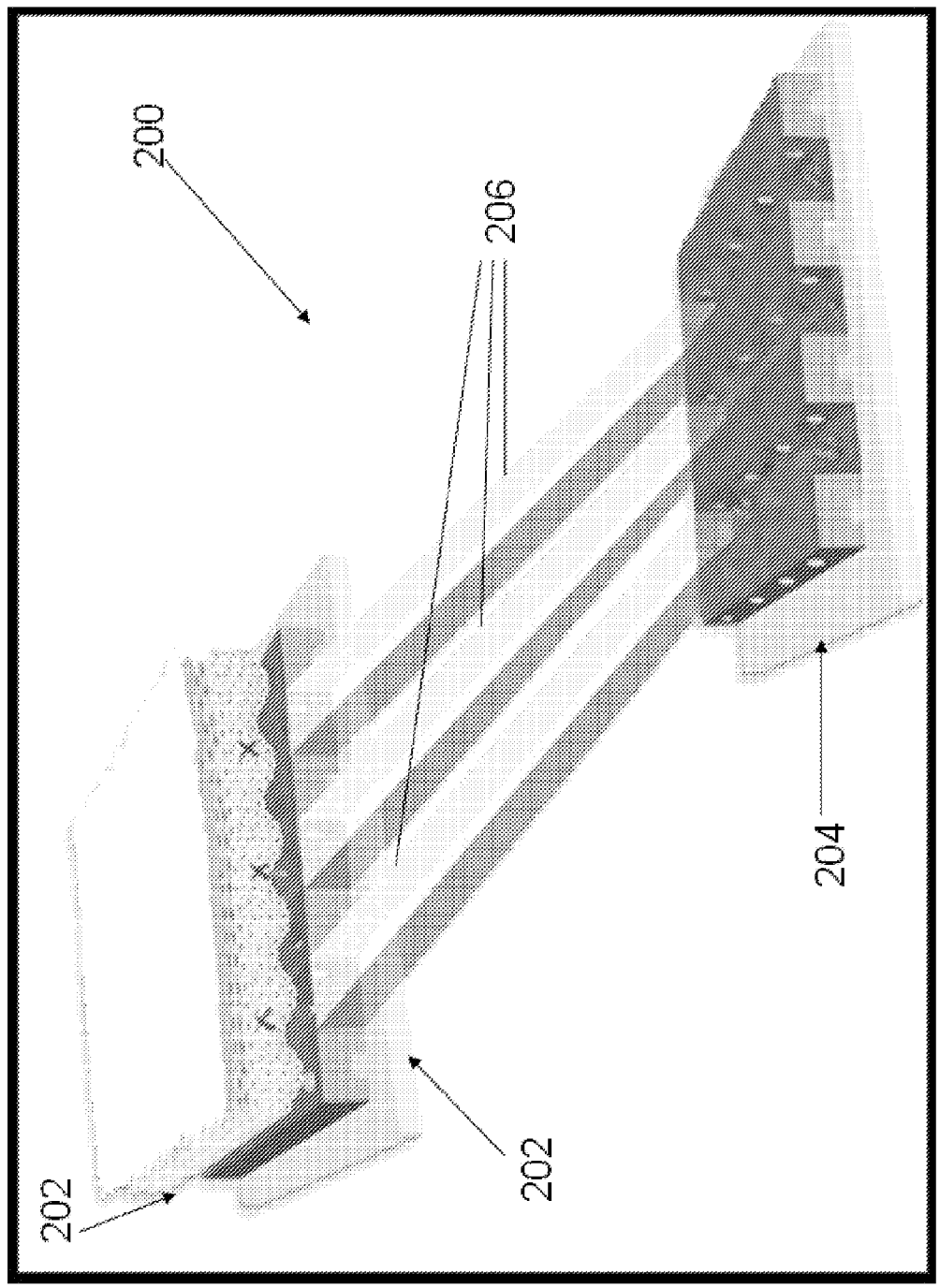
FIG. 2 is a perspective view of one embodiment the immune modeling system.
Figure 3:
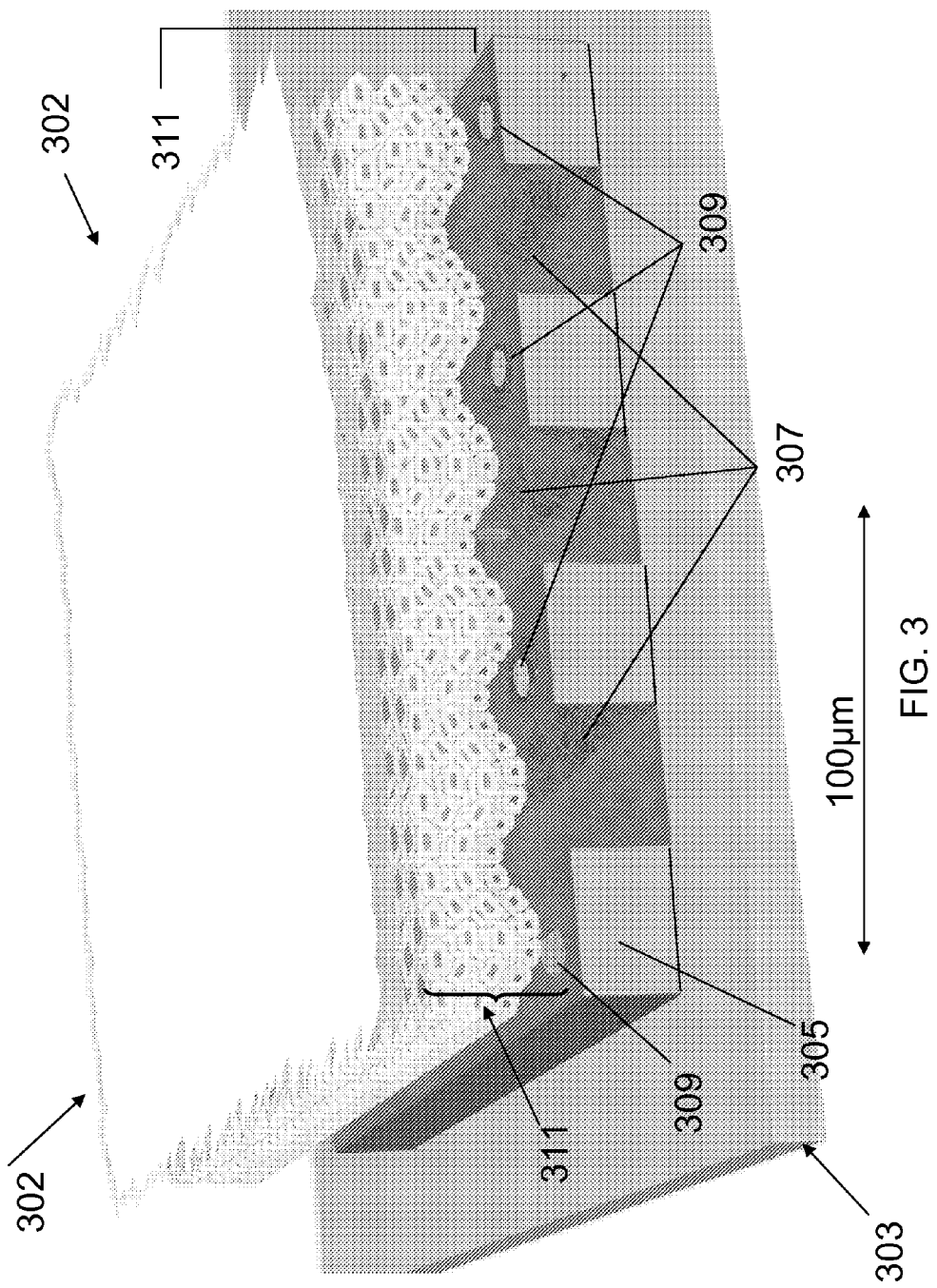
FIG. 3 is a perspective view of the barrier component of an immune modeling system.

As illustrated in FIG. 2, immune modeling device 200 can include a three-dimensional barrier component 202 in fluid communication with a three-dimensional immune component 204. As shown, inter-compartment microfluidics 206 can provide fluid communication between barrier component 202 and immune component 204. The details of one embodiment of barrier component 202 are illustrated in FIG. 3. In an embodiment, the immune modeling device further comprises an optical observation component configured to view cell movement within the device. The cell movement can be the movement of immune cells, such as dendritic cells, from one compartment to another compartment. The observation component can be optically transparent. In an embodiment, the observation component is the inter-compartment microfluidics 206. In another embodiment, the observation component further comprises an imaging component in contact or optical communication with the immune modeling device. For example, a CCD camera, a microscope, a CMOS sensor, or a photodiode could be used as an imaging component to observe the movement of immune cells from one compartment to another. In an embodiment with either a plurality of barrier compartments 202 or a plurality of immune compartments 204, a device can include a plurality of observation components.

In some embodiments, a single immune system module may be utilized; however, it is very useful to be able to rapidly screen a large number of substances, via a high throughput screen, for their physiological impact on biological barriers. In some embodiments, the immune modules are prepared as a microarray to present a number of immune modules on a single platform or chip. One can utilize one, two, 10, 12, 20, 24, 50, 70, 96, 100, 384, or 1536, or any number of individual immune modules on a single platform or chip. With such arrays the immune modeling device described herein can be prepared in a high throughput format for screening potential sensitization or toxicity with living cells as a surrogate testing system for animals The microarray of the immune modeling device can have various embodiments with a variety of components of the modules at an addressable location on the chip. For example, an individual component of the device described herein, such as a barrier component or an immune component, can comprise a unit of an array or a complete immune module may represent a single unit of many presented on the microarray. A barrier component in fluid communication with an immune component via one or more observation components can comprise a unit of an array. Multiple biological barrier components in fluid communication with multiple immune components via one or more observation components can comprise a unit of an array. Many biological barriers components may be configured in microchannel communication with one or a few immune components or one or a few biological barriers may be configured in microchannel communication with many immune components. In one embodiment, the array is monitored to measure the combined response of multiple test agents separately or individually applied to separate biological barriers which feed to a single immune component. In this manner one can test for the combined effect of a number of substances but still segregate some of the effects of each individual test agent.

Efficient delivery of media to cells on the array can be facilitated by a microfluidic system harnessed to control the flow rate of each unit of the array independently. The system may be controlled to provide different flow rates to individual modules of the microarray utilizing valves and sensors in the system. The system may include a feedback monitoring system to control the delivery of media customized for the metabolic needs of the immune modules.

FIG. 3 illustrates a barrier component 302 of an immune modeling device. A barrier component 302 can include a substrate 303. Examples of a substrate 303 include, but are not limited to, glass, polymer, silicon, and metal. The substrate 303 can include a material that is amenable to the growth of cells. A substrate 303 can include a single or plurality of media access channels 305. In another embodiment, media access channels 305 are located on a surface of substrate 303. The shape of media access channels 305 can be a square tube, as illustrated in the exemplary embodiment of FIG. 3, or any other shape as would be obvious to one skilled in the art. Space between a plurality of media access channels 305 or the edges of an immune modeling device can include at least one immune component access channel 307. Immune component access channels 307 can be in fluidic communication with an immune component of a device.

In an embodiment, a media access channel 305 can include a single or plurality of fluidic vias 309, from which media can be provided to a biological barrier 311. It is envisioned that a media access channel 305 can have a plurality of fluidic vias 309, and in some embodiments, have a plurality of fluidic vias 309 on the surface of a media access channel 305. A biological barrier 311 can include any biological entity, such as connective tissue and epithelial cells. In an embodiment, a biological barrier 311 includes epithelial cells. It is also envisioned that biological barrier 311 can further comprise at least one of epidermal tissue and dermal layer. In another embodiment, dermal tissue is located between epidermal tissue and media access channels 305. A biological barrier 311 can comprise fibroblasts. In another embodiment, a biological barrier 311 includes dendritic cells, such as Langerhans cells. In yet another embodiment, a polymer matrix is located between a biological barrier 311 and media access channels 305 (not shown). The matrix can be attached to the substrate of the barrier component and can serve, for example, as an attachment feature for the biological barrier.

Figure 4:
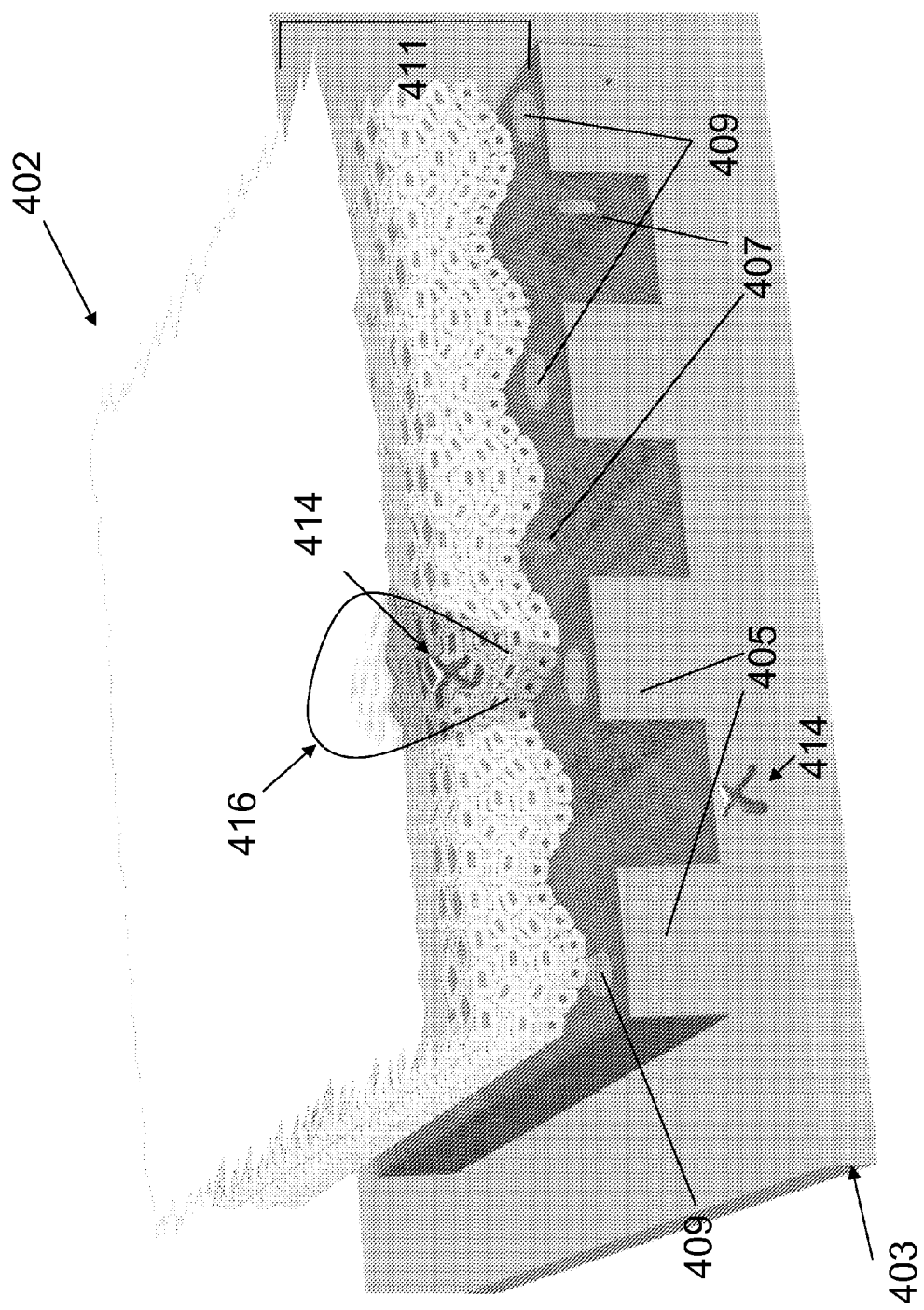
FIG. 4 is a perspective view of the barrier component of an immune modeling system including immune cells and a gradient.

FIG. 4 illustrates another exemplary embodiment of a barrier component 402 of an immune modeling device. The figure illustrates fluidic vias 409 in a plurality of media access channels 405 located on a substrate 403. Media can be provided to a biological barrier 411 by a media access channel 405. Area and/or volume between a plurality of media access channels 405 is shown as an immune component access channel 407 in the exemplary embodiment in FIG. 4. A biological barrier 411 can comprise a phagocyte such as a dendritic cell 414 that can be cultured with and be capable of traveling away from the biological barrier 411. An exemplary dendritic cell is a Langerhans cell. A substance gradient 416 affecting dendritic cells can be formed within the biological barrier 411 such that dendritic cells 414 move away from the barrier. For example, a substance can be brought into contact with the surface of the biological barrier 411 that creates a response within the barrier wherein the dendritic cells 414 move away from the barrier. In another embodiment, a gradient 416 is formed in the biological barrier 411 by putting the layer into communication with an attractant, wherein the attractant creates a gradient 416 in which dendritic cells 414 move away from a biological barrier 411. In an embodiment, dendritic cells 414 travel within immune component access channels 407 away from the biological barrier 411.

Figure 5:
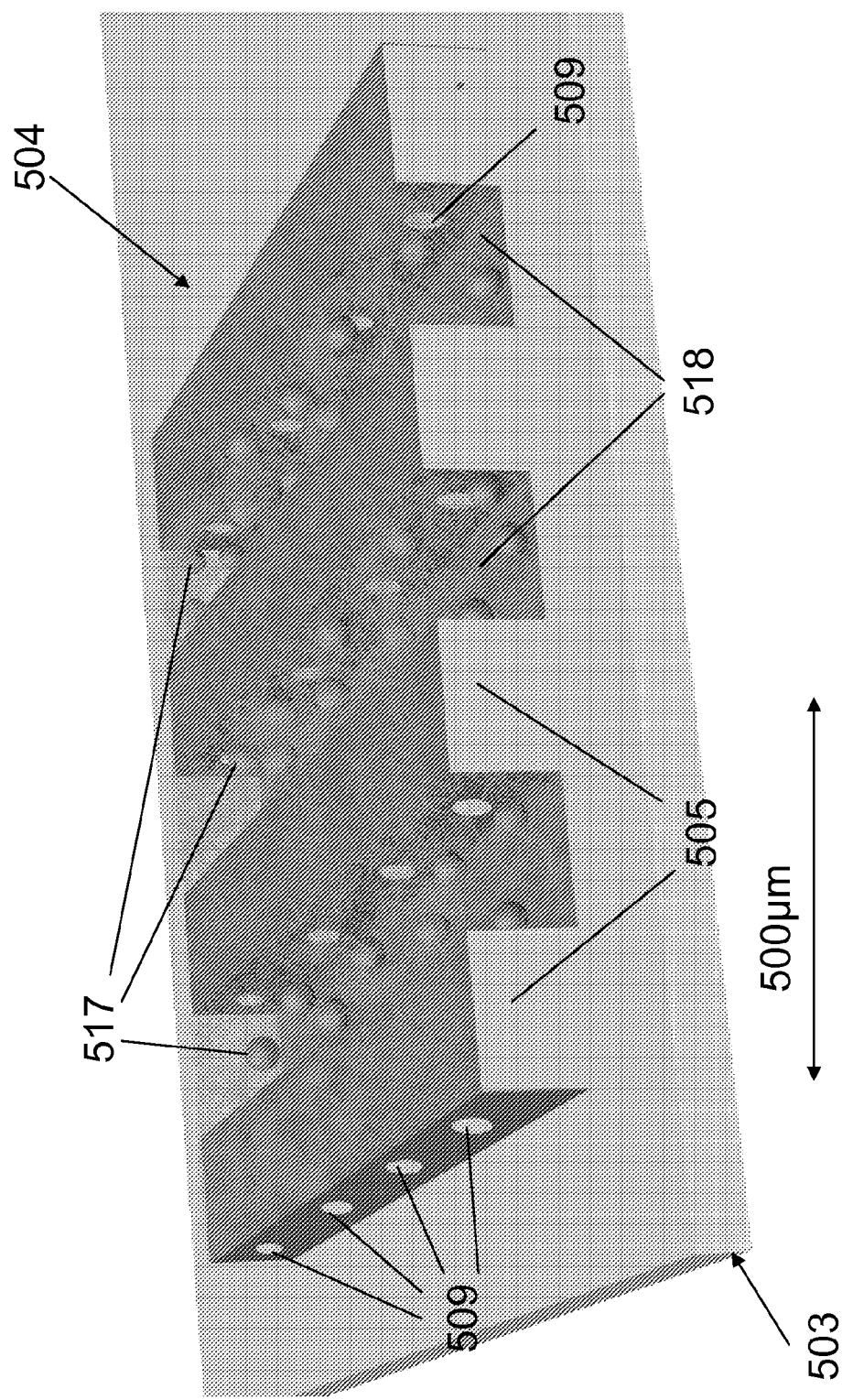
FIG. 5 is a perspective view of the immune component of an immune modeling system including immune cells.

FIG. 5 illustrates an exemplary immune component 504 of an immune modeling device. In an embodiment, an immune component 504 includes a substrate 503 and at least one media access channel 505. A media access channel 505 can comprise a single or a plurality of fluidic vias 509 through which media can flow away from the channel. Immune cells (T-cells or immune lymph node cells) 517 can be cultured in fluidic communication with the media access channels 505 and/or substrate 503. In an embodiment, T-cells or immune lymph node cells 517 are attached to the substrate 503 or media access channels 505. In another embodiment substrate 503 includes a matrix as discussed above regarding the barrier component. The area or volume between a plurality of media access channels 505 or the edges of the substrate can include a single or a plurality of T-cell compartment or lymph node compartment channels 518.

Figure 6:
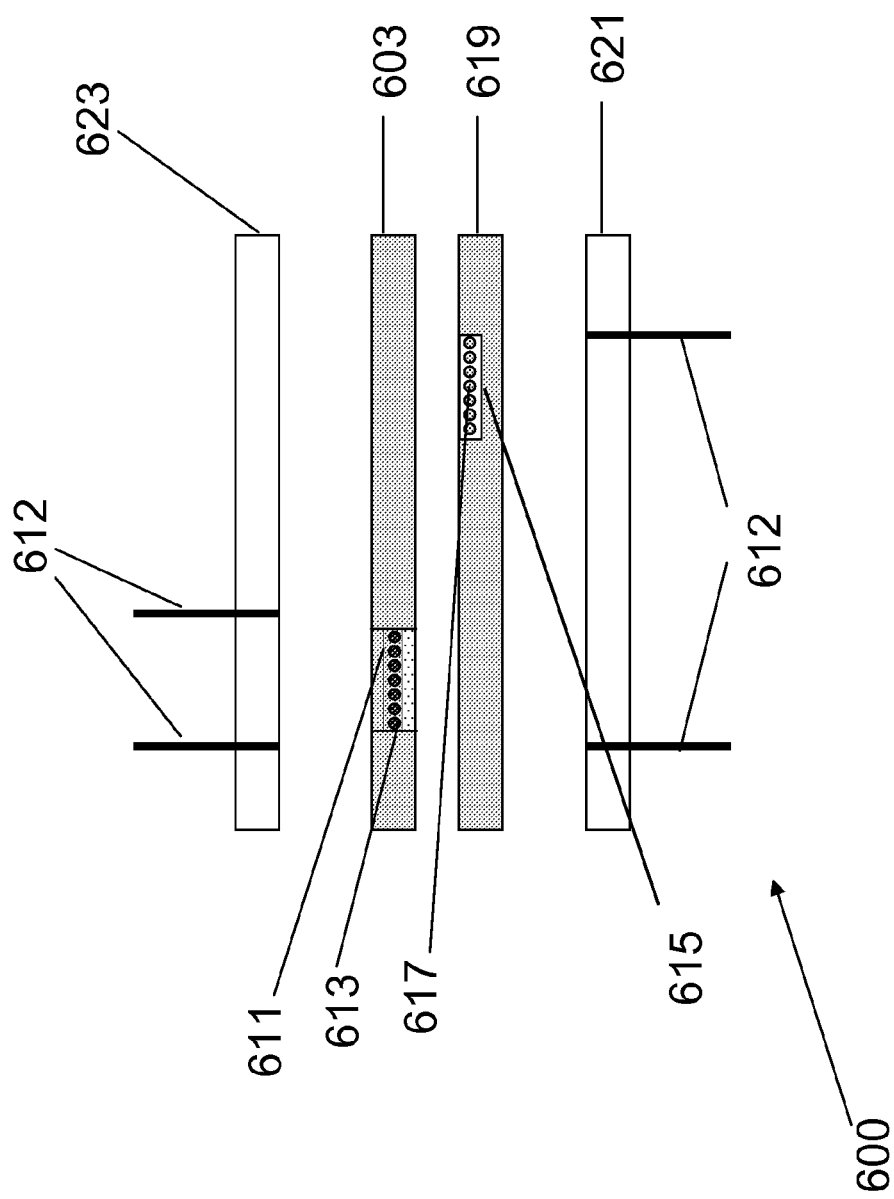
FIG. 6 is a cross-section of one embodiment of the immune modeling system.

An embodiment of an immune modeling device 600 is demonstrated in FIG. 6. The exemplary device includes a barrier compartment including a biological barrier 611 and barrier substrate 603, an immune compartment 615 including an immune substrate 619 and immune cells (T-cells or immune lymph node cells) 617, a barrier compartment interface 623, an immune compartment interface 621, and microfluidics 612. In this exemplary embodiment, immune modeling device 600 includes a plurality of layers that can be used to construct the device. The barrier compartment is part of or attached to a separate substrate (barrier substrate 603) than the immune compartment (immune substrate 619). The substrates can comprise the same or a different material. In an embodiment the substrates are adhered to one another. In another embodiment the substrates are in fluidic communication with one another.

Figure 7:
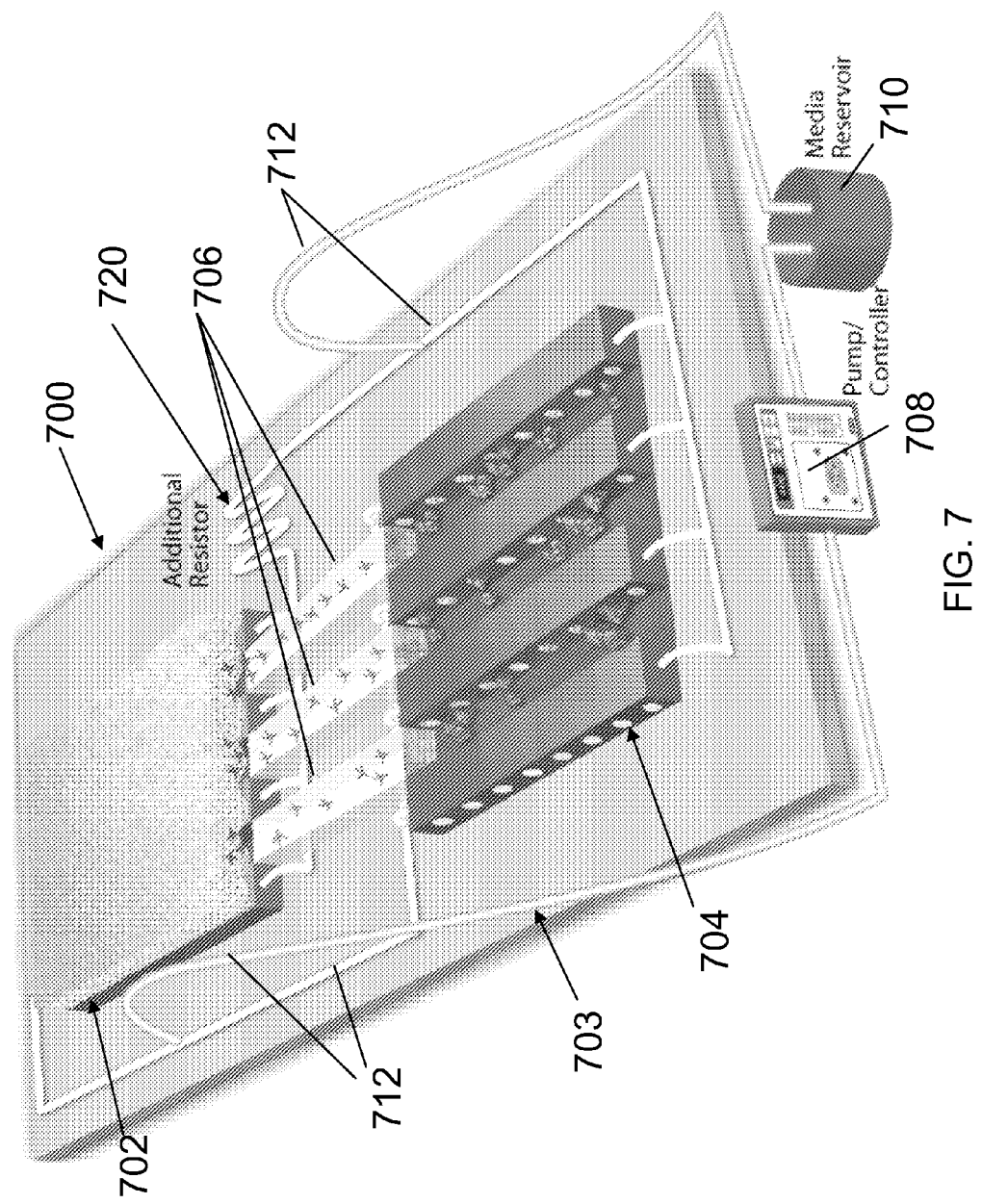
FIG. 7 is a perspective view of an integrated embodiment of the immune modeling system including a pump a controller and a reservoir.

FIG. 7 illustrates an aspect described herein of an integrated immune modeling system 700 including a barrier component 702 in fluidic communication by way of inter-component microfluidics 706 with an immune component 704. In an embodiment, an integrated system 700 is located on or as part of a substrate 703. A system can also comprise a pump 708 for providing fluid from a reservoir 710 to components of the system through microfluidics 712. Examples of fluid useful in an integrated immune modeling system 700 include, but are not limited to, cell culture media. In an embodiment, microfluidics 712 connect media access channels of a component to a reservoir 710, wherein the reservoir 710 can provide media to the channels and the component by means of pump 708. In another embodiment, microfluidics 712 provide media to a component of a system by capillary action. Microfluidics 712 for providing liquid to component may comprise a fluidic resistor 720 in order to affect fluid flow as desired.

In an embodiment, such as the exemplary embodiment in FIG. 7, an integrated immune modeling system 700 is utilized to model an immune system reaction. For example, a layer of a biological barrier, such as epithelium, can be cultured or placed onto a barrier component 702 and provided with media through microfluidics 712, in order to maintain the health of the biological barrier. A biological barrier can be epithelium, such as artificial skin, including an epidermis and a dermis, wherein the epithelium can be exposed to the environment to more closely simulate skin on a human body. In one embodiment the artificial skin is maintained on a semi-permeable membrane. In order to model the immune system, a test substance can be applied to the surface of a biological barrier, which in turn causes the immune cells, such as dendritic cells, within the biological barrier to activate or migrate (or be induced to migrate using, e.g., using an attractant or repellent substance) away from the biological barrier. The dendritic cells can come into fluidic communication with an immune component 704 of a system. An immune component 704 can comprise attractive immune system cells, such as T cells to model an in vivo immune system. As a gradient of dendritic cells is formed moving from one component to the other, dendritic cell movement can be measured or observed to determine the immune reaction of the substance applied to the biological barrier. Alternatively T cell proliferation may be measured as a result of dendritic cell activation.

In one embodiment, a detection method of the immune modeling device described herein comprises the rate of chemotaxis of the dendritic cells coupled with the measurement of T cell activation. The rate of chemotaxis can be measured by the number of cells migrating toward the immune component while T cell activation can be measured by the degree of cell proliferation or the extent to which T cell derived cytokines are secreted. Fluorescent-based cell labeling can be utilized to quantitate such level of proliferation, for example. By coupling the rate of chemotaxis with the rate or degree of T cell activation, the immune modeling device described herein can provide information on the relative sensitization potential and/or the concentration of the sensitizer test agent producing the cellular responses. Also by coupling the rates, it is possible to determine a threshold level of the test agent that triggers the cellular responses. A more accurate and dynamic evaluation is performed utilizing an analysis of both parameters. For example, various concentrations of a substance can be applied to the biological barrier component and the concentration-dependent changes in cellular dynamics, such as, rate of response, between dendritic cell migration and T-cell activation can be quantitated. Such analysis enhances the determination of the sensitization potential and/or the threshold level of test agents that may be tolerated in a preparation for in vivo use. In one embodiment, one measures the rate of migration of the migrating cells and the rate of the proliferation of the T-cells. Alternatively, one can measure the amount of both the migration of the migrating cells (numbers of cells migrating) and the level of proliferation of the T-cells.

Examples of a test substances potentially producing an immune reaction in an integrated immune modeling system 700 include, but are not limited to, drugs, cosmetics, nutraceuticals, synthetic chemicals, fragrances, lubricants, soaps, shampoos, hair products, sunscreens, lotions, and oils.

The biological barrier may be cells from any biological barrier, such as, skin, cornea, lining of the lungs, lining of the gastrointestinal tract, lining of the genitourinary tract, or artificial skin comprising cultured keratinocytes.

With any of the biological barriers, it is possible to screen test agents and identify hypersensitivity reactions. For example, one can utilize cells from the cornea as the biological barrier in the test device. Similarly, cells from the gastrointestinal tract may be employed as the biological barrier in a device to screen test agents for sensitivity in conditions, such as, inflammatory bowel disease, Crohn's disease, ulcerative colitis, ulcerative proctitis, or primary sclerosing cholangitis. Selection of the specific cells from different physiological regions of the body to form the biological barrier enables one to tailor the screening process and analyze hypersensitivity of test agents with respect to various diseases or conditions and various biological systems.

Keratinocyte "Artificial Skin" Component:

One objective of the described embodiments is to provide an artificial skin as model of a viable epidermis. To achieve such an artificial skin standard techniques as known in the art for keratinocyte culture can be used. In one example primary keratinocytes can be derived from human foreskin samples and layered cultures can be developed by raising submerged cultures to the air-liquid interface. In another example, reconstructed skin models may alternatively be used. For example, REALSKIN FT or EpiSkin as described by SkinEthic Laboratories can be used (see http://www.skinethic.com/_int/_en/index.aspx; web site last visited Jan. 4, 2009). Markers for proliferation and differentiation (e.g. Ki67, involucrin, etc.) can be used to monitor/track the keratinocytes growth and development.

A number of features of the artificial skin can be assessed including but not limited to assessment of barrier function (e.g., through permeability studies), assessment of metabolism and assessment of maturation of the layered tissue of the artificial skin. Barrier function of the artificial skin can be assessed, for example, by either simple addition to the cell's culture medium or topical application via dye-saturated filters placed atop the artificial skin. Barrier function can be assessed, for example, by monitoring the permeability of fluorescent dyes at several stages of development from keratinocyte monolayers to a 3-dimensional layered epidermis. Dye permeability can be determined, for example, with an HPLC approach using non-fluorescent dyes or by confocal microscopy with fluorescent dyes. Metabolism in skin layers can be monitored, for example, using compounds containing a primary amino group (e.g., p-aminobenzoic acid, benzocaine, and azo color reduction products) along with control, non-metabolizing compounds such as, for example, benzo[a]pyrene and/or 7-ethoxycoumarin.

Dendritic Cell/T Cell Component:

Another objective of the invention is to provide a dendritic cell and/or T cell component as a model of immune system component interaction with a barrier layer. In one embodiment a compartment, cell, chamber or channel is provided for culturing dendritic cells and visualizing their migration by time-lapse microscopy using, for example, an inverted microscope, equipped with DIC objectives, epifluorescent illumination, and a CCD camera. It is envisioned that using the devices described herein it is possible to observe migrating activated dendritic cells. For example, dendritic cells could be observed microscopically as they migrate from a cultured artificial skin barrier layer. Observation could occur at any or all of the barrier component, the inter-component microfluidic connections and the immune component.

In a particular embodiment, the dendritic cells are chemotactically directed to a compartment, cell, chamber or channel including other immune cells (e.g., T cells) for downstream allogeneic stimulation. In this embodiment the two cell types can be cultured in separate compartments, cells, chambers or channels that are interconnected. It is envisioned that the interconnection can be any form of fluidic connection including but not limited to a channel, microchannel, tube, vessel or the likes. The number or cell types culture and interconnected should not be limited to just two. It is envisioned that a plurality of immune system cellular components (e.g., three or more, four or more, etc.) can be cultured in configurations that provide desired interactions between cell types.

In addition to or instead of dendritic cells, it is envisioned that other phagocytic cell types, for example, macrophages and/or neutrophils can be as described herein for dendritic cells to study immune system component interaction with a barrier layer.

Allogeneic stimulation of dendritic cells by T cells can be assessed, for example, using fluorescence methods well known in the art. The analysis of the migration of cells and the proliferation of the T-cells may be evaluated through a variety of methods. In one embodiment, optically transparent regions are provided in the device to visually observe the cells. There may be one or more such optical windows integrated into the device at various locations including in the first compartment, second compartment and one or more of the inter-connecting microfluidic channels. Using a microscope, one can observe the rate and number of migrating cells and the rate or number of proliferating T-cells In other embodiments, the device described herein can utilize other methods to identify biomarkers useful for indicating the effect of a substance on one or more biological barriers. Dendritic cells migrating out of barrier component can be characterized by analytical methods known in the art. Useful analytical methods include methods typically used for analyzing the level of RNA expression, the content of genetic material, the compositions of glycoproteins and biological materials produced by the cell. Non-limiting examples of analytical methods include polymerase chain reaction, DNA sequencing, southern blotting, northern blotting, western blotting, microarray, 2D electrophoresis, and immunoassays.

In one embodiment, a substance in question is applied to a biological barrier component, the migrating dendritic cells are collected or otherwise identified outside or inside the biological barrier component, and characteristics of the migrating cells can be determined. For example, one could analyze the protein expression profile of the cells collected therefrom. The protein profile is compared to a protein profile representative of normal or resting dendritic cells and the proteins differentially expressed or uniquely associated with said collected dendritic cells are identified as biomarkers. In another embodiment, the biomarkers identified by the device described herein are provided to indicate the presence of a substance in a level substantially detectable by dendritic cells. In yet another embodiment, the level of a biomarker is related to a predictive value by which the relative sensitization potential of a substance is indicated. An evaluation of the level of activation of the migrating dendritic cells can be done to give a screen for the test agent and its effects on the biological barrier component. In one embodiment the device may include just the biological barrier with migrating dendritic cells and the migrating dendritic cells may be evaluated for activation.

In one embodiment, the immune component of the device may comprise T-cells along with other cells, such as cells that exist in the lymph nodes. In another embodiment, the immune component comprises just T-cells without any additional cells in the compartment at the beginning of the analysis. The T-cells may be cultured as a 2-D layer on a conventional support or matrix formulated to facilitate cell growth or the T-cells may be cultured in suspension of a culture medium using conventional culture techniques known in the art. During the analysis, dendritic cells from the biological barrier compartment or layer may migrate into the immune compartment or layer.

Advantageously, in one embodiment the system provides for locking (or focusing) a concentration gradient of molecules, agents or compounds (e.g., of a chemotactic agent) on a moving cell. To achieve this, in a particular embodiment a gradient can be established in a microfluidic channel with the added capability of adjusting in real time the position and slope of the gradient. In a related embodiment control of the system can be provided by including a computer controller that, for example, adjusts the position and slope of the gradient with the changing location and shape of the moving cell. Through such computer control, it is possible to achieve a feed-back system that can decouple the temporal and spatial components of chemokine stimulation. It is further envisioned that the slope and position of a concentration gradient on a moving cell can be controlled inside a microfluidic channel using a system of on-chip valves. The valves can be controlled by computer through a feed-back loop that can include, for example, the physical displacement of the cell, the change in shape of the cell during directional migration, or the level of expression of fluorescently tagged molecules involved in the signaling process.

The dendritic cells provided can be derived from human blood as well as dendritic-type cell lines like MUTZ-3 which can be induced to mature (e.g. express CD83, CD1a, etc.). Migrating cells can be monitored for morphological changes, and can be probed for levels of maturation, antigen uptake, antigen presentation, and/or T cell activation.

By way of one non-limiting example, the gradient molecules can be the chemokine ligands (CCL19)/MIP3-β and CCL21/SLC, two chemokines constitutively expressed by lymph nodes (LN) and other immune cells, which share a common chemokine receptor, CCR7.

Fabrication of Immune Modeling Systems

In one embodiment, the immune module may be a relatively simplistic construct of a first culture compartment culturing the biological barrier cells and optionally also dendritic cells, a second compartment culturing immune or lymphatic cells, such as, just T-cells as the lymphocytes, and one or more microfluidic channels connecting the first and second compartments to permit fluidic communication between compartments and the migration of cells. The construction of the immune module and the inclusion of only a single lymphatic cell type contribute to an effective analytical device which very quickly provides the ability to screen in vitro a number of test agents for their potential in vivo use. The use of a single lymphatic cell type without the complication of many systems in the immune module provides efficient functioning and rapid screening of test agents. In an alternative embodiment, the immune module comprises only a few lymphatic cell types.

By way of one non-limiting example the starting material or substrate for manufacturing the immune modeling devices and systems described herein can be a wafer usually made of Silicon (Si) or Silica (SiO2). The most common wafer diameters in use are 4", 6" and 8". The manufacturing process for a barrier component, immune component and inter-component microfluidics involves two basic processes namely, deposition and etching. A short description of each of them is given below.

In certain embodiments the methods of manufacturing the systems described herein can include, but are not limited to laser writing, UV writing and photonic band-gap waveguide methods. The manufacturing process in some embodiments includes one or more steps of deposition, masking and etching.

Deposition

In the deposition step a layer of well defined material having well controlled thickness is deposited across the entire wafer. The most common material used for microfluidic layer deposition is Silica (SiO2) also known as glass. Other materials such as silicon, glass, epoxy, lithium niobate, indium phosphide and SiON (Silicon OxyNitride) and its derivatives are also used.

The deposition step is done using several technologies such as PECVD (Plasma-Enhanced Chemical Vapor Deposition), LPCVD (Low Pressure CVD), APCVD (Atmospheric pressure CVD), FHD (Flame Hydrolysis Deposition) and others well known in the art.

Masking

Following the deposition and before the etching step, the desired two-dimensional structure of the immune modeling device is transferred to the deposited wafer by masking the areas not to be etched away. The masking is done in several steps involving covering the wafer with light sensitive material, exposing it to light through lithographic masks and removing the exposed material leaving in place the mask.

Etching

In the etching step, material at the un-masked areas is removed from the top core 1023 layer of the substrate. The etching rate is a known parameter, therefore the etching depth can be controlled by time. The two most common techniques for etching are wet-etching and Reactive-Ion-Etching (RIO).

After the etching step, an over-cladding or top cladding 1029 layer is created using a deposition step similar to the one described above. The above steps can be repeated to create several layers one on top of the other as needed.

When the wafer processing is completed, it can be diced into individual chips.

System Control

Figure 8:
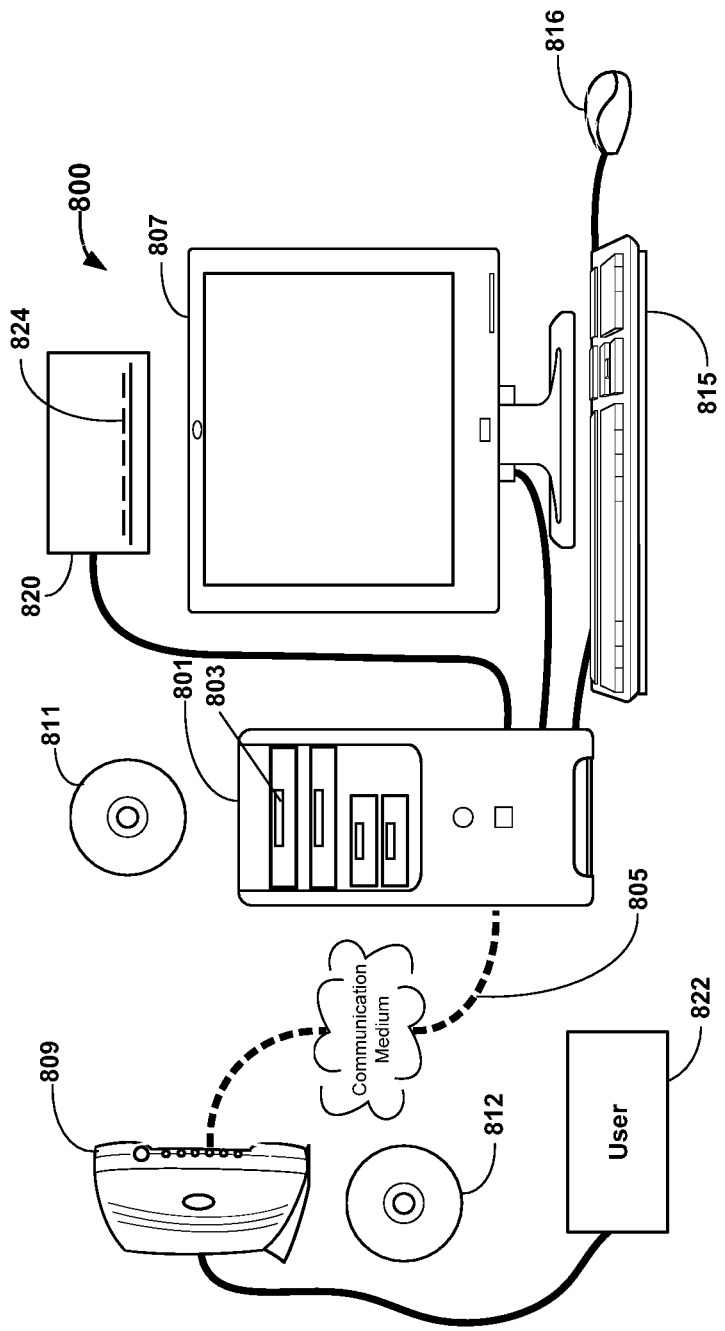
FIG. 8 is a block diagram showing a representative example logic device in communication with an apparatus for use with the scanning sensing system of the invention.

In an aspect, a device or system described herein can be operated or controlled by a user. As illustrated in FIG. 8, a user can be in communication with a device or system using a computer. The user interface of the computer may include a keyboard, mouse, and monitor. The computer can be in communication with the device through a hard-line connection, such as Ethernet, Fire Wire, USB, or other connections, or can be in wireless communication with the device, such as over a wireless network or Bluetooth. The computer can comprise a hard-disk for storing information from a device or system and can comprise a method of writing data to a storage device such as a flash memory drive, a CD-ROM, or a DVD.

Data Analysis

In some embodiments a condition, for example, an allergic, autoimmune, and/or inflammatory condition, is detected in a biological barrier test sample (e.g., a skin sample) subjected to an agent, compound, formulation or composition. In a further embodiment, a measured result of analyzing the agent, compound, formulation or composition effect on the test sample can be used to diagnose a condition or disease state of a patient. In yet another embodiment the detection method of the invention can further include a method of diagnosing a condition or disease state. In a related embodiment, the method of diagnosing a disease can include reviewing or analyzing data relating to the detection of a condition or disease state and providing a conclusion to a patient, a health care provider or a health care manager, the conclusion being based on the review or analysis of data regarding a condition or disease diagnosis. Reviewing or analyzing such data can be facilitated using a computer or other digital device and a network as described herein. It is envisioned that information relating to such data can be transmitted over the network.

FIG. 8 is a block diagram showing a representative example logic device through which reviewing or analyzing data relating to the present inventions can be achieved. Such data can be in relation to a disease, disorder or condition in a subject. FIG. 8 shows a computer system (or digital device) 800 connected to an apparatus 820 for use with the immune modeling system 824 to, for example, produce a result. The computer system 800 may be understood as a logical apparatus that can read instructions from media 811 and/or network port 805, which can optionally be connected to server 809 having fixed media 812. The system shown in FIG. 8 includes CPU 801, disk drives 803, optional input devices such as keyboard 815 and/or mouse 816 and optional monitor 807. Data communication can be achieved through the indicated communication medium to a server 809 at a local or a remote location. The communication medium can include any means of transmitting and/or receiving data. For example, the communication medium can be a network connection, a wireless connection or an internet connection. It is envisioned that data relating to the present inventions can be transmitted over such networks or connections.

In one embodiment, a computer-readable medium includes a medium suitable for transmission of a result of an analysis of a biological test sample. The medium can include a result regarding a condition or disease or state of a subject, wherein such a result is derived using the methods described herein.

Kits

Kits including reagents useful for performing the methods described herein are also provided.

In some embodiments, a kit includes reagents including an immune modeling system, culture media, and other components as described herein.

The kit may optionally contain one or more of the following: one or more of the immune modeling systems, one or more cell cultures that can be cultured in the systems, and various chemokines, cytokines, growth factors, etc.

The components of a kit can be retained by a housing. Instructions for using the kit to perform a described method can be provided with the housing, and can be provided in any fixed medium. The instructions may be located inside the housing or outside the housing, and may be printed on the interior or exterior of any surface forming the housing that renders the instructions legible. A kit may be in multiplex form for testing a plurality of test samples and/or a plurality of agents.

Figure 9:
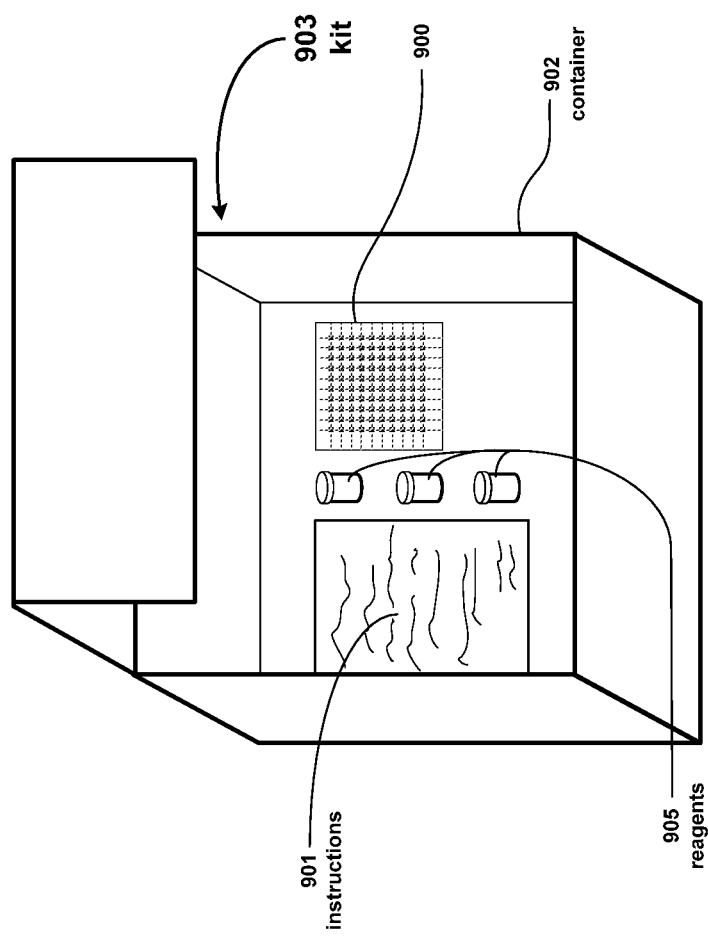
FIG. 9 is a block diagram showing a representative example of a kit.

As described herein and shown in FIG. 9, in certain embodiments a kit 903 can include a container or housing 902 for housing various components. As shown in FIG. 9, and described herein, in one embodiment a kit 903 including one or more immune modeling systems 900, and optionally reagents 905 are provided. As shown in FIG. 9, and described herein, the kit 903 can optionally include instructions 901. Other embodiments of the kit 903 are envisioned wherein the components include various additional features described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of determining whether of a test agent induces a hypersensitivity reaction, comprising:
   providing a hypersensitivity modeling device, comprising
      i) a first culture compartment containing a biological barrier and comprising dendritic cells;
      ii) a second culture compartment containing T-cells; and
      iii) one or more inter-compartment microfluidic connections between said first and second compartments, configured to permit the migration of dendritic cells from said first compartment to said second compartment;
   culturing said biological barrier, dendritic cells, and T-cells within said device;
   flowing culture media between said compartments;
   applying a test agent to said biological barrier; and
   measuring at least one feature of a hypersensitivity reaction in an immune cell in the device to determine whether there is an increase in the at least one feature of a hypersensitivity reaction after application of the test agent;
   wherein, if an increase in the at least one feature of a hypersensitivity reaction in an immune cell in the device is measured after application of the test agent, the test agent is determined to induce hypersensitivity reaction.

2. The method of claim 1, wherein if an increase in at least one feature of a hypersensitivity reaction in an immune cell in the device is not measured after application of the test agent, the test agent is determined to not induce hypersensitivity reaction.

3. The method of claim 1, wherein the at least one feature of a hypersensitivity reaction is selected from:
 i) the rate of T-cell proliferation;
 ii) the amount of T-cell proliferation;
 iii) the rate of dendritic cell migration; and
 iv) the amount of dendritic cell migration.

4. The method of claim 3, wherein the at least one feature of a hypersensitivity reaction is the rate of T-cell proliferation.

5. The method of claim 3, wherein the at least one feature of a hypersensitivity reaction is the amount of T-cell proliferation.

6. The method of claim 3, wherein the at least one feature of a hypersensitivity reaction is the rate of dendritic cell migration.

7. The method of claim 3, wherein the at least one feature of a hypersensitivity reaction is the amount of dendritic cell migration.

8. The method of claim 1, wherein an increase in the at least one feature of a hypersensitivity reaction in an immune cell is measured in the presence of the test agent and the test agent is determined to induce a hypersensitivity reaction.

9. The method of claim 1, wherein an increase in the at least one feature of a hypersensitivity reaction in an immune cell is not measured in the presence of the test agent and the test agent is determined to not induce a hypersensitivity reaction.

10. The method of claim 1, wherein said biological barrier is cultured skin.

11. The method of claim 1, wherein said biological barrier is cultured cornea.

12. The method of claim 1, wherein said biological barrier is cultured lining of the lungs.

13. The method of claim 1, wherein said biological barrier is cultured lining of the gastrointestinal tract.

14. The method of claim 1, wherein said biological barrier is cultured lining of the genitourinary tract.

15. The method of claim 1, wherein said biological barrier is cultured artificial skin.

16. The method of claim 15, wherein the biological barrier is cultured artificial skin comprising cultured keratinocytes.

17. The method of claim 1, wherein said biological barrier comprises a dermal layer.

18. The method of claim 1, wherein said at least one feature of a hypersensitivity reaction is a feature of delayed type contact hypersensitivity.

19. The method of claim 1, wherein said test agent comprises a drug, cosmetic, nutriceutical, synthetic chemical, fragrance, lubricant, soap, shampoo, hair product, sunscreen, lotion or oil.

20. The method of claim 3, wherein the migration of said dendritic cells is monitored through an optical observation component located in said first or second compartment or one or more of said fluidic connections.

21. A method of determining that a test agent induces a hypersensitivity reaction, comprising:
 providing a hypersensitivity modeling device, comprising
  i) a first culture compartment containing a biological barrier and comprising dendritic cells;
  ii) a second culture compartment containing T-cells; and
  iii) one or more inter-compartment microfluidic connections between said first and second compartments, configured to permit the migration of dendritic cells from said first compartment to said second compartment;
 culturing said biological barrier, dendritic cells, and T-cells within said device;
 flowing culture media between said compartments;
 applying a test agent to said biological barrier; and
 measuring an increase in at least one feature of a hypersensitivity reaction in an immune cell in the device, the at least one feature selected from:
  i) the rate of T-cell proliferation;
  ii) the amount of T-cell proliferation;
  iii) the rate of dendritic cell migration; and
  iv) the amount of dendritic cell migration;
 to thereby determine that the test agent induces a hypersensitivity reaction.

22. A method of determining that a test agent does not induce a hypersensitivity reaction, comprising:
 providing a hypersensitivity modeling device, comprising
  i) a first culture compartment containing a biological barrier and comprising dendritic cells;
  ii) a second culture compartment containing T-cells; and
  iii) one or more inter-compartment microfluidic connections between said first and second compartment, configured to permit the migration of dendritic cells from said first compartment to said second compartment;
 culturing said biological barrier, dendritic cells, and T-cells within said device;
 flowing culture media between said compartments;
 applying a test agent to said biological barrier; and
 determining that at least one feature of a hypersensitivity reaction does not occur in an immune cell in the device, the at least one feature selected from:
  i) the rate of T-cell proliferation;
  ii) the amount of T-cell proliferation;
  iii) the rate of dendritic cell migration; and
  iv) the amount of dendritic cell migration;
 to thereby determine that the test agent does not induce a hypersensitivity reaction.

* * * * *